United States Patent
Barlow

(10) Patent No.: US 6,589,756 B1
(45) Date of Patent: *Jul. 8, 2003

(54) IMMUNOASSAYS USING ANTI-ALLOTYPIC MONOCLONAL ANTIBODIES

(75) Inventor: Eve H. Barlow, Holliston, MA (US)

(73) Assignee: Bayer Corporation, Medfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/662,987

(22) Filed: Sep. 15, 2000

Related U.S. Application Data

(63) Continuation of application No. 09/076,940, filed on May 13, 1998, now Pat. No. 6,146,836.
(60) Provisional application No. 60/046,962, filed on May 19, 1997.

(51) Int. Cl.[7] .................. G01N 33/53; G01N 33/543; G01N 33/563; C07K 16/00; C12P 21/08
(52) U.S. Cl. .................. 435/7.92; 435/7.1; 435/7.21; 435/7.9; 435/7.94; 436/63; 436/501; 436/513; 436/518; 436/523; 436/527; 436/532; 436/536; 530/386; 530/387.1; 530/387.9; 530/388.1; 530/388.15
(58) Field of Search .................. 435/7.1, 7.9, 7.94, 435/7.21, 7.92; 436/532, 513, 518, 501, 523, 527, 536, 63; 530/386, 387.1, 387.9, 388.1, 388.15

(56) References Cited

U.S. PATENT DOCUMENTS

| | | | |
|---|---|---|---|
| 4,048,298 A | | 9/1977 | Niswender .................. 424/1.5 |
| 4,539,292 A | | 9/1985 | Reid et al. .................. 435/7 |
| 4,745,181 A | | 5/1988 | Law et al. .................. 530/387 |
| 5,063,165 A | | 11/1991 | Hu et al. .................. 436/506 |
| 5,219,730 A | * | 6/1993 | Potocnjak et al. .......... 435/7.93 |
| 5,223,426 A | | 6/1993 | Skibbens et al. ....... 435/240.27 |
| 5,227,489 A | | 7/1993 | Law et al. .................. 546/23 |
| 5,241,070 A | | 8/1993 | Law .................. 546/107 |
| 5,256,541 A | * | 10/1993 | Pouletty et al. ............. 435/7.24 |
| 5,395,752 A | | 3/1995 | Law et al. .................. 435/6 |
| 5,783,453 A | * | 7/1998 | Barlow et al. .............. 436/518 |

FOREIGN PATENT DOCUMENTS

| | | |
|---|---|---|
| EP | 0440044 A1 | 1/1991 |
| WO | WO9505468 | 2/1995 |
| WO | WO 97/01763 A1 * | 1/1997 |

OTHER PUBLICATIONS

Bona, et al., "Anti–immunoglobulin antibodies IV. Cross–reaction of anti–idiotypic antibodies specific for rabbit and murine anti–al allotypic antibodies with Fc fragment of human immunoglobulins", European Journal of Immunology 14:548–552 (1984).

Catty, et al., "The Effect of Polyethylene Glycol (PEG) on Precipitation of Mouse and Rabbit Immunogloubulin Allotypes in Microradioimmunoassays," Immunochemistry 11: 615–618 (1974).

Dresser, et al., "Immunoglobulin Allotypes of the Mouse", Biochemical Society Transactions 560th Meeting, Oxford 4:34–38 (1976).

Herzenberg, et al., "Mouse Immunoglobulin Allotypes: Characterization and Use In Cellular Immunology", Ann. Immunol. 125C:71–83 (1974).

Huang, et al., "Genetic Characterization of Mouse Immunoglobulin Allotypic Determinants (Allotupes) Defined by Monoclonal Antibodies," Immunogenetics 18:311–321 (1983).

Kohler, et al., "Continuous cultures of fused cells secreting antibody of predefined specificity ," Nature 256:495 (1975).

Oi, et al., "Localization of Murine Ig–Ib and Ig–Ia (IgG 2a) Allotypic Determinants Detected with Monoclonal Antibodies," Molecular Immunology 16:1005–1017 (1979).

Parsons, et al., "A Monoclonal Mouse Antiallotype Antibody Reacts with Certain Human and Other Vertebrate Immunoglobulins: Genetic and phylogenetic Findings," Immunogenetics 12:207–219 (1981).

Tijssen, P. "The Immobilization of Immunoreactants on Solid Phases," Laboratory Techniques in Biochemistry and Molecular Biology, vol. 15, Chapter 13:297–328 (1985); and.

Zhou, et al. "A Dehydroepiandrosterone Sulfate (DHEA–S) Assay on the Automated Chemiluminescent System ACS:180" Clinical Chemistry, Abstract No. 351, vol. 43:S183 (1997).

* cited by examiner

Primary Examiner—Long V. Le
Assistant Examiner—Kartic Padmanabhan
(74) Attorney, Agent, or Firm—Palmer & Dodge LLP.

(57) ABSTRACT

The invention provides improved immunoassay techniques for detecting the presence of analytes in a liquid sample. The present immunoassay methods utilize anti-allotypic monoclonal antibodies as capture reagents for primary binding proteins specific for the analytes of interest. The monoclonal antibodies are highly specific for the allotypic determinants present on the primary binding protein. The use of anti-allotypic monoclonal antibodies as capture reagents provides improved levels of specificity and accuracy of the immunoassay, in part because interference from endogenous immunoglobulins in the sample is significantly reduced. The invention further provides anti-allotypic monoclonal antibodies.

24 Claims, 3 Drawing Sheets

Binding curves— IgG2a Mabs and anti-allotype solid phase

Dehydroepiandrosterone sulfate (DHEA-S) immunoassay—Normalized binding curves

IMMUNOASSAYS USING ANTI-ALLOTYPIC MONOCLONAL ANTIBODIES

RELATED APPLICATIONS

This application is a continuation of U.S. Ser. No. 09/076,940, filed May 13, 1998, now U.S. Pat. No. 6,146,836, which claims benefit of U.S. Ser. No. 60/046,962, filed May 19, 1997.

BACKGROUND OF THE INVENTION

The present invention relates to immunoassays for an analyte, such as a drug, hormone or an antigen, in a liquid sample, such as body fluid. More particularly, the present invention relates to a method for the detection of an analyte in a body fluid using anti-allotypic monoclonal antibodies as capture reagents or as detector reagents.

Many types of ligand-receptor assays have been used to detect the presence of various substances in body fluids such as urine or blood serum. These assays typically involve antigen-antibody reactions and synthetic conjugates comprising enzymatic, fluorescent, chemiluminescent, or radioactive labels. In most of these assays, there is a receptor (e.g. an antibody) which is specific for the selected ligand (e.g., analyte or antigen), and a means for detecting the presence and/or amount of the antigen-antibody reaction product. Most current tests are designed to make a quantitative determination, but in some circumstances all that is required is a positive/negative indication.

These immunoassays must be very sensitive because of the often small concentration of the ligand of interest in the test fluid. However, test samples of body fluids contain numerous components, some of which can interfere with the immunoassay. For example, endogenous immunoglobulins or complement proteins present in the sample may react with the test immunoglobulins, causing misleading results. Immunoglobulins or complement proteins present in the sample may react with capture antibodies, analyte-specific binding proteins (which can be primary antibodies) which are part of the immunoassay, thereby preventing attachment of the analyte to the binding protein, and/or attachment of the binding protein to the antibodies (which can either be labeled or attached to a solid phase). Additionally, complement proteins in the test sample may bind to analyte-antibody complexes formed during the test and prevent attachment of the binding proteins to the capture or labeled antibodies. When the assay results are read and interpreted, they may indicate an incorrectly high or low concentration of analyte, depending on the assay format used. Such incorrect results may lead a physician to improperly diagnose a disease state, or prescribe an incorrect course of treatment. Because of these problems, competitive immunoassays, sandwich immunoassays and other immunological detection methods utilize various techniques to reduce interferences. However, these techniques have not solved all of the problems encountered in these detection methods. It is an object of the present invention to provide an improved immunoassay having less sensitivity to endogenous components in the sample and greater accuracy and discrimination for analytes of interest.

SUMMARY OF THE INVENTION

The present invention provides rapid, sensitive immunoassay methods for detecting the presence of analytes in body fluids. The methods have high sensitivity and accuracy, and less sensitivity to the presence of endogenous immunoglobulins and complement proteins in the sample. Use of the present methods provide immunoassays which reproducibly yield reliable results.

The present invention provides a method for improving the accuracy of an immunoassay for determining the amount of analyte in a patient sample, in particular, samples from human patients. The present method improves the accuracy and specificity of the results obtained from the immunoassay by reducing or eliminating the assays' sensitivity to endogenous immunoglobulins and complement proteins in the sample. The method comprises providing as a capture reagent or as a detectable label an antibody specific for an allotypic determinant on a primary binding protein used to detect the analyte of interest. The primary binding protein typically is not attached to a solid phase, whereas the capture antibody typically is attached to a solid phase. However, in some assay formats, the primary binding protein may be bound to an antigen on a solid phase and detected by a labeled antibody. The patient sample can be, for example, blood serum or plasma, urine, lymphatic fluid or cerebrospinal fluid.

In one embodiment, the method comprises (a) combining the patient sample with (i) a primary binding protein specific for the analyte, and (ii) a known amount of detectably labeled tracer molecules specific for said binding protein; (b) incubating the combination under conditions sufficient to permit the analyte and the tracer molecules to competitively bind to the binding protein; (c) contacting the combination with a solid phase having immobilized thereon an allotype-specific capture antibody specific for the primary binding protein allotype; (d) incubating the combination under conditions sufficient to permit the binding protein to bind with the capture antibody; (e) separating the solid phase from the sample; and (f) detecting the amount of labeled tracer molecules bound to the solid phase. In this method, the analyte competes with the labeled tracer molecule for binding sites on the binding protein. Therefore, the greater the concentration of analyte present in the sample, the fewer tracer molecules will bind to the binding protein. The resulting signal is inversely proportional to the amount of analyte in the sample. The amount of analyte present can be determined by comparing the results obtained to a standard curve.

In another embodiment, both the primary binding protein and the anti-allotypic capture antibody may be free in the sample. In this embodiment, the anti-allotypic capture antibody may be conjugated with a capturable species, e.g., biotin. The primary binding protein, the anti-allotypic antibody and a known amount of labeled tracer are combined with the sample. The tracer can be either the actual analyte or a fraction or analog thereof which has a comparable affinity for the binding protein. The mixture is incubated for a time sufficient to permit the analyte or tracer molecule to bind with the binding protein. The mixture then is contacted with a solid phase having immobilized thereon a capture component specific for the capturable species, e.g., where the capturable species is biotin, the capture component can be avidin or streptavidin. The solid phase then is separated from the sample, and the signal is measured as described above. The use of an affinity couple, such as avidin-biotin, to immobilize the capture monoclonal antibody can be utilized in any of the different assay formats described herein.

Variations of the basic assay are possible. For example, the primary binding protein can be added to the reaction mixture separate from the allotype specific antibody which is attached to a solid phase. Alternatively, the analyte analog, which could be the analyte itself, can be attached to a solid phase to compete with the analyte from the sample for complexing the primary binding protein, which, when reacted with the labeled allotype-specific antibody, will yield, after separation of the solid phase, a labeled complex which can be measured. Furthermore, in each of these methods, several reagents can be premixed. For example, the anti-allotype reagent can be premixed with the primary binding protein before reaction with the patient sample.

The method of the invention may be designed to exploit conventional sandwich assay formats or other immunoassay formats. For example, in one embodiment of a sandwich technique, the primary binding protein binds to the analyte of interest to form a complex. This complex then binds to the immobilized capture protein which, in this embodiment, comprises a second antibody specific for an allotypic determinant on the binding protein, to form an immobilized capture protein-primary binding protein-analyte complex, which is then reacted with a labeled antibody to form a "sandwich". The solid phase containing the bound complex then is removed from the sample, and the amount of label is determined.

The invention further comprises reagents for carrying out the method. In one aspect, the reagent comprises a solid phase having immobilized thereon anti-allotypic monoclonal antibodies specific for an allotypic determinant on an analyte-specific primary antibody.

In another aspect the invention comprises anti-allotypic monoclonal antibodies for use as capture or secondary antibodies in immunoassay methods.

The use of anti-allotypic monoclonal antibodies enables construction of a family of extremely sensitive assay systems which minimize interference by endogenous immunoglobulins and complement proteins present in the sample.

BRIEF DESCRIPTION OF THE FIGURES

The present invention will now be more particularly described with reference to and as illustrated in, but in no manner limited to, the accompanying drawings, in which.

DETAILED DESCRIPTION OF THE INVENTION

Figure 1:
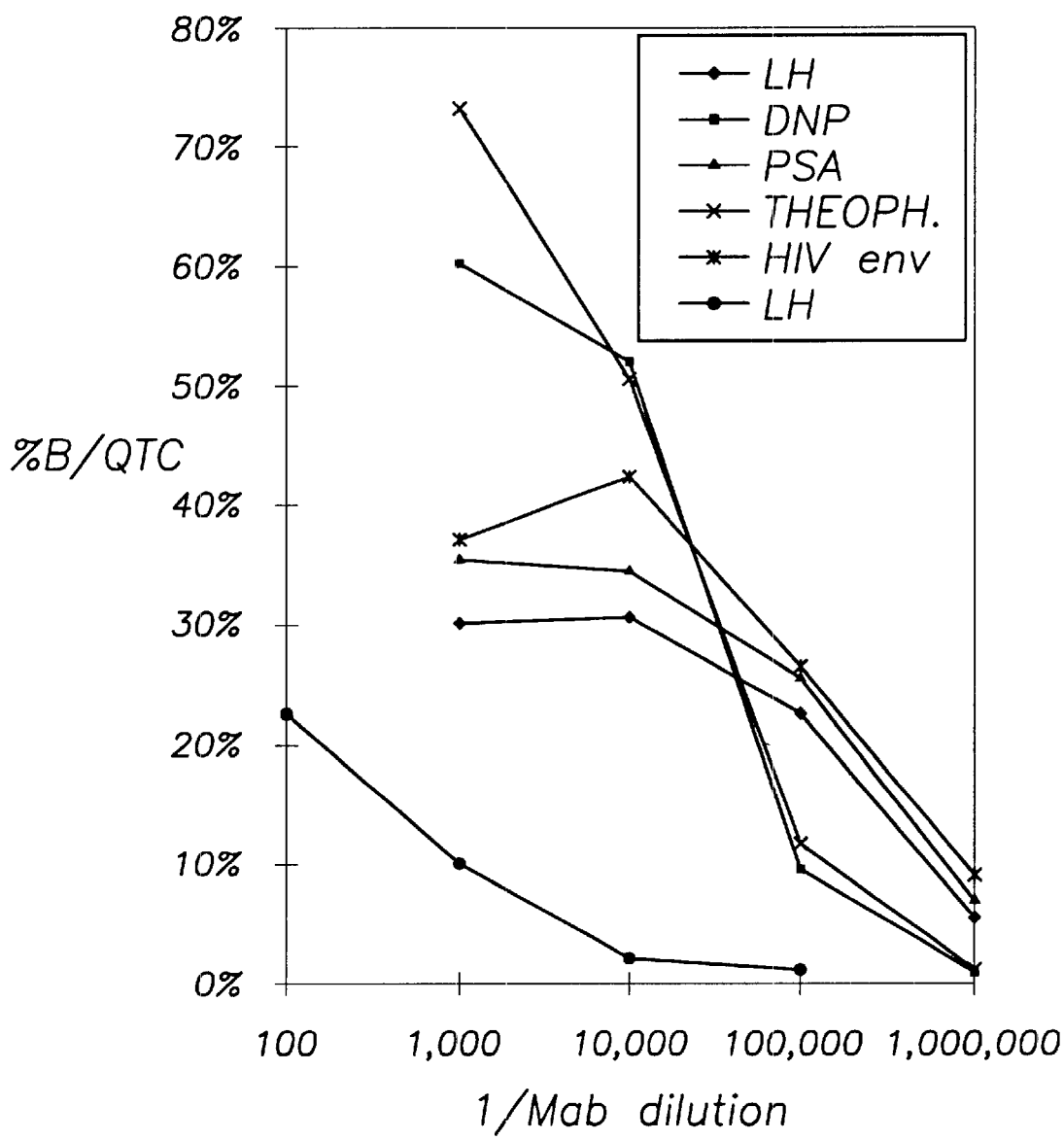
FIG. 1 is a graph illustrating the binding curves for various primary antibodies of the $IgG_{2a}$ for binding to anti-allotypic $IgG_{2a}$-specific monoclonal antibodies immobilized on a solid phase.

The method of the invention involves the use of monoclonal anti-allotypic antibodies to achieve accurate, reproducible indication of the presence of an analyte, such as a drug or hormone, in a test sample from a patient. The method and device may be used to detect the presence of analytes in liquid samples such as blood serum or plasma, cerebrospinal fluid, lymphatic fluid, urine, mucus or other body fluid, or in a tissue in a histoimmunoassay.

The immunoassay methods of the invention enable one to reliably assay a liquid or tissue sample for the presence of extremely small quantities of a particular analyte, while avoiding interference from endogenous immunoglobulins or complement proteins in the sample. Broadly, the method of the invention can be used to detect any analyte which has heretofore been assayed using known immunoassay procedures, or is detectable by such procedures, using polyclonal or monoclonal antibodies, fragments thereof, or other binding proteins. Various specific assay formats or protocols, reagents, and analytes useful in the practice of the invention are known per se.

The feature believed to be responsible for the excellent sensitivity and reproducibility of assays conducted in accordance with the invention is the use of anti- allotypic antibodies as capture reagents for capturing analyte-specific primary binding proteins or labeling reagents for detecting analyte-specific primary binding proteins. The allotype-specific antibodies are highly specific for an allotypic determinant on the primary binding protein.

The present immunoassays generally are conducted by contacting a primary binding protein, which is specific for the analyte of interest, with the body fluid, tissue sample or other test material. The primary binding protein preferably is a monoclonal antibody, but may be an antibody fragment, a receptor or an engineered protein having the necessary analyte binding properties and an allotypic determinant which can be recognized by the capture antibody.

In a preferred embodiment, the primary binding protein is a monoclonal antibody, a fragment of a monoclonal antibody, or a single chain antibody or binding site having comparable affinity for the analyte. The primary binding protein may be an immunoglobulin of subtype G, M, A or E. In a currently preferred embodiment, the primary binding protein is an immunoglobulin G isotype. The primary binding protein must contain at least one allotypic determinant. The term "allotypic determinant" as used herein is defined as an immunologically active epitope, site or region of a macromolecule, e.g., an immunoglobulin, which occurs in some but not all, members of the same species. The complex formed by the analyte and binding protein then reacts with a capture anti-allotypic antibody.

The capture, or secondary, anti-allotypic antibody is highly specific for the allotypic determinant(s) on the primary antibody. The capture antibody preferably is a monoclonal antibody, which does not need to be of the same isotype as the primary binding protein. In a currently preferred embodiment, the capture antibody is immobilized on a solid phase. A complex forms at the capture site comprising the immobilized anti-allotypic monoclonal antibody-binding protein-analyte. The primary binding protein and the capture anti-allotypic antibody may be derived from any suitable species, such as, for example, mouse, rabbit, goat, sheep, guinea pig or human. The antibody also may be chimeric. In a currently preferred embodiment, both the primary binding protein and the capture antibody are mouse monoclonal antibodies.

Monoclonal antibodies or fractions thereof having specific binding properties and high affinity for the analyte of interest which are useful in the present invention as primary binding proteins either are known and commercially available, or can be produced from stable cell lines using well known cell fusion and screening techniques. The literature is replete with protocols for producing and immobilizing proteins. See, for example, *Laboratory Techniques in Biochemistry and Molecular Biology.* Tijssen, Vol. 15, Practice and Theory of Enzyme immunoassays, chapter 13, The Immobilization of Immunoreactants on Solid Phases, pp. 297–328, and the references cited therein.

Anti-allotypic monoclonal antibodies also may be obtained by well known methods including those referenced above. The anti-allotypic monoclonal antibody also may be of any suitable species, or may be chimeric, but must be specific for the species and subtype of an allotypic determinant on the primary binding protein. Allotype-specific monoclonal antibodies thus must be raised to recognize a particular allotypic determinant present on the primary binding protein. This can be accomplished by careful selection of the antigen used to raise the antibodies and the host animal. In one embodiment, anti-allotypic monoclonal antibodies are produced according to the following protocol:

Protein A-purified murine monoclonal antibodies derived from a particular mouse strain (e.g., IgG2a from A/J strain or $IgG_1$ from SJL strain) are coupled to keyhole limpet hemocyanin (KLH). Host mice of a different strain are immnunized with the resulting immunogen. For example, SJL mice are immunized with the $IgG_{2a}(Igh1^a)$-KLH conjugate; and A/J mice are immunized with $IgG_1(Igh4^b)$-KLH conjugate. Each mouse typically receives a total of about three immunizations. The final immunization is administered about four days before cell fusion.

Cell fusions are performed using spleen cells from immunized mice and SP2-0 myeloma cells, according to methods described by Kohler and Milstein (*Nature,* vol. 256, pp. 495 (1975)). Hybridoma supernatants are screened for anti-allotypic monoclonal antibodies, for example, using a chemiluminescent assay. In this embodiment, supernatants were tested for their ability to link an acridinium ester labeled monoclonal antibody that was the same isotype and came from the strain of mouse as the immunizing monoclonal antibody to a paramagnetic particle, onto which a third monoclonal antibody, of the same isotype and from the same mouse strain as the immunizing monoclonal, had been immobilized. The specificity of the anti-allotypic monoclonal antibodies can be confirmed by determining the effect on inking tracer and solid phase monoclonals when the isotype and strain of IgG subtype origin was varied from those of the immunizing monoclonal antibody.

Interference in the immunoassay also may be caused by endogenous complement proteins in the sample. Complement proteins present in the sample may bind to the primary binding protein, particularly when the primary binding protein is an antibody, thus preventing attachment of the primary binding protein to the capture antibody. Interference by complement proteins may be minimized by utilizing an anti-allotypic antibody that does not bind to part of the primary antibody's complement binding site. It is known that Clq, the first protein of the complement cascade, binds to the CH2 region of IgG. By selecting an anti-allotypic antibody that binds to the CH3 domain, analyte-primary antibody-complement complexes, which may form in the sample, will still be captured by such an anti-allotypic antibody immobilized on a solid phase.

In a currently preferred embodiment of the present invention, both the primary antibody and the allotype-specific antibody are of mouse origin, preferably of an IgG subtype.

From the foregoing, it will be apparent that the success of the test procedure is dependent both on analyte present in the sample reacting with the primary binding protein, or on reproducible competition between the analyte and the tracer molecules for sites of attachment on the primary binding protein, and on the specificity of the primary binding protein for the capture allotype-specific monoclonal antibody.

In order to detect the amount of analyte in a sample, a component having a detectable label is included in the assay. The detectable label can be, for example, a chemiluminescent compound, a fluorescent compound, an enzyme or a radioisotope. In the currently preferred embodiment, chemiluminescent acridinium-ester labels are used, such as those described in U.S. Pat. Nos. 4,745,181; 5,227, 489; 5,241, 070; and 5,395,752.

In a currently preferred embodiment, the immunoassay of the present invention is designed to detect the concentration of a drug or hormone in the bloodstream of a patient. In this embodiment, the binding protein is a monoclonal antibody. against the drug or hormone. Anti-allotypic monoclonal antibodies which can be used as capture antibodies are those having specificity for an allotypic determinant on the primary antibody. In other embodiments, the assay may be adapted to detect for other analytes such as, for example, infectious agents.

The capture anti-allotypic monoclonal antibody preferably is immobilized on a solid substrate to facilitate separation of the reaction complex formed by the primary binding protein and the anti-allotypic monoclonal antibody. Any solid phase can be used, for example, magnetic particles, beads, membranes including chromatography paper, filter paper and nitrocellulose paper, trays or test tubes. Methods for immobilizing antibodies to solid substrates are well known per se, and do not form a part of this invention.

In a preferred embodiment, the invention further comprises the step of adding to the reagent mixture antibodies having an allotype which is different from the binding protein allotype, and which is therefore not recognized by the capture monoclonal antibody. The amount of added antibody preferably is an excess over the amount of primary binding protein. The addition of these antibodies further reduces interference in the assay by endogenous immunoglobulins or complement proteins present in the sample. For example, many humans have present in their bloodstreams and tissues human anti-mouse immunoglobulins (HAMA), the origin of which is uncertain. HAMA may interfere with, and affect the results of, immunoassays which utilize murine antibodies performed on samples from these humans. For example, immunoassays often are used for determining serum levels of a therapeutic drug in a patient. HAMA in the patient's serum may interfere with the assay, causing the results to show an incorrectly high or low level of the drug in the patient. A physician relying on these results then accordingly may decrease or increase the dosage of drug to the patient, which could have adverse effects, such as an increase in side effects or toxicity, or reduced efficacy. The present immunoassay methods provide reduced sensitivity to HAMA, and thus, better accuracy and reproducibility. The present invention also may be used when antibodies against other species other than mouse are present in the patient sample, for example, human anti-rabbit antibodies, which may interfere with immunoassays using rabbit antibodies.

The added antibodies preferably are derived from the same mouse strain used to produce the capture antibody, and preferably have the same isotype as the primary binding protein. In a currently preferred embodiment, the added antibody is preincubated with the patient sample prior to addition of the primary binding protein to the sample.

In a currently preferred embodiment of the present invention, the amount of analyte in a patient sample is determined according to the following method: the patient sample is preincubated with an excess (over the amount of primary antibody) of IgG antibodies having the same isotype as the primary antibody, and derived from the same strain of mouse used to produce the capture antibody. After preincubation, the sample is combined with a primary monoclonal antibody and a tracer comprising acridinium-ester labeled analyte molecules specific for the primary antibody, and the resulting combination is incubated under conditions sufficient to permit any analyte in the sample and the tracer analyte to bind to the primary antibody. The sample then is contacted with paramagnetic particles having immobilized thereon capture anti-allotypic monoclonal antibodies which are specific for the primary antibody allotype, and incubating the mixture of the particles and sample under conditions sufficient to permit the primary antibody to bind with the capture antibody. The particles then are removed from the sample and washed to remove any unbound tracer and unbound analyte. The amount of acridinium-ester label then is determined, and the amount of detected label is correlated to standard binding curves to determine the amount of analyte which was present in the sample.

The amounts of the various reagents used to carry out the immunoassays of the invention will depend upon the titer of the antibodies used, and can easily be empirically determined by the skilled practitioner. One skilled in the art would know how to titrate the reagents and determine the relative amounts necessary to perform the immunoassays without requiring any undue experimentation.

The present invention will now be further particularly described with reference to the following Examples, which are not intended to be limiting in any way. In the Examples, the invention is described with reference to FIGS. 1–3 of the accompanying drawings which have been briefly described hereinabove.

Example 1

Production of Anti-Allotypic Monoclonal Antibodies

Purpose: To develop hybridoma cell lines that produce monoclonal antibodies that are specific for allotypes of mouse $IgG_{2a}$, ($Igh1^a$) and mouse $IgG_1(Igh4^b)$.

Methods

Preparation of immunogens: Protein A-purified monoclonal antibodies ($IgG_{2a}$ from A/J strain or $IgG_1$ from SJL) were coupled to KLH (keyhole limpet hemocyanin) using glutaradehyde at a ratio of 2 mg of IgG/2 mg of KLH.

Immunization of mice: Mice were immunized intraperitoneally at monthly intervals with 100 ug of the immunogens. The first injection was done with Complete Freund's adjuvant; subsequent injections were done with Incomplete Freund's adjuvant. SJL mice were immunized with the $IgG_{2a}(Igh1^a)$-KLH conjugate; A/J mice were immunized with $IgG_1(Igh4^b)$-KLH conjugate. Each mouse received a total of three immunizations. The final immunization, in saline, was administered intravenously and intraperitoneally four days before cell fusion.

Cell fusions: Fusions were done using spleen cells from immunized mice and SP2-0 myeloma cells, according to methods described by Koter and Milstein. G. Kohler and C. Milstein, *Nature*, 256:495 (1975).

Screening of hybridoma supernatants: Hybridoma supernatants were screened for anti-allotypic monoclonal antibodies using a chemiluminescent assay. Supernatants were tested for their ability to link an acridinium ester labeled monoclonal, that was the same isotype and came from the strain of mouse as the immunizing monoclonal antibody, to a paramagnetic particle, onto which a third monoclonal antibody, of the same isotype and from the same mouse strain as the immunizing monoclonal, had been immobilized. Specificity of anti-allotypic monoclonal antibodies was confirmed by determining the effect on linking tracer and solid phase monoclonals when the isotype and strain of IgG origin was varied from those of the immunizing monoclonal antibody.

Results and Discussion

Anti-allotypic monoclonals were developed and shown to be specific. Clone 229-2D1.2A10 (deposited at American Type Culture Collection and identified as deposit number ATCC HB-12350) reacts with $IgG_{2A}$ Mabs from A/J and Balb/c mice. Clone 240-10C12.1C12.2F11 (deposited at American Type Culture Collection and identified ad ATCC HB-12349) reacts with $IgG_1$ from SJL and ICR mice. Both cell lines were deposited Apr. 29, 1997, in compliance with the Budapest Treaty. The address of American Type Culture Collection as of Mar. 23, 1998 is 10801 University Boulevard, Manassas, Va. 20110-22099.

Testing Anti-allotype Solid Phase 229-2D1.2A10 with Monoclonal Antibodies of Varied Specificity Purpose: To demonstrate that anti-allotype PMP using monoclonal 220-2D1.2A10, which is specific for $IgG_{2a}$ from strains bearing $Igh1^a$ allotype, can react with $IgG_{2a}$ monoclonals from A/J and Balb/c mice.

Materials and Methods

Monoclonal Antibodies used

| ID# | Strain | IgG subcl. | Specificity | Form | Source |
| --- | --- | --- | --- | --- | --- |
| 73-2H1 | Balb/c | $IgG_{2a}$ | LH | Ascites | Chiron Diagnostics |
| 69-5H1 | A/J | $IgG_{2a}$ | DNP | Ascites | Chiron Diagnostics |
| 256-10A12 | A/J | $IgG_{2a}$ | PSA | Supernat. | Chiron Diagnostics |
| 90-1A11 | A/J | $IgG_{2a}$ | Theophyl. | Ascites | Chiron Diagnostics |
| 274-11E9 | Balb/c | $IgG_{2a}$ | HIV env. | Ascites | Chiron Diagnostics |
| MIL0101 | Balb/c | $IgG_{2a}$ | LH | Purified | Medix Biotech. |

Antibodies were diluted in PBS, 0.1% BSA.

Tracers: Acridinium ester (AE) labeled tracers were used: LH-AE, DNP-BSA-AE, PSA-AE, Theophylline-AE, HIV env-AE. Tracers were diluted in PBS, 0.1% BSA.

Solid phase: 229-2D1.2A 10 coupled to paramagnetic particles (PMP) was diluted to 200 ug PMP/ml.

Assay: 100 $\mu$l of monoclonal antibody and 100 $\mu$l of tracer were incubated together for 1 hour at room temperature. 500 $\mu$l of PMP was added and incubated 10 minutes at room temperature. Particles were magnetically separated and washed twice with PBS, 0.05% TritonX-100. Particles were resuspended in 100 $\mu$l of water and counted in an MLA 2.

Results and Discussion

Binding curves were obtained for all the primary monoclonal antibodies tested, regardless of their specificity. See FIG. 1. Differences in maximum binding obtained are indicative of different primary monoclonal antibody affinities and specific activities of the acridinium ester labeled tracers used.

The specificity of the anti-allotype monoclonal antibody, 229-2D1.2A10, was confirmed, as this antibody coupled to a solid phase could bind to immune complexes of Balb/c and A/J $IgG_{2a}$ Mabs and their specific antigens.

Example 2

Theophylline Immunoassay using Anti-allotype Solid Phase

The following protocol utilizes an anti-allotype monoclonal antibody coupled to paramagnetic particles to separate bound analyte from free analyte using a theophylline immunoassay as a model. The performance of the anti-allotype monoclonal antibody is compared to polyclonal goat anti-mouse Ig a as the secondary or capture antibody.

Materials and Methods

Reagents

Primary anti-theophylline monoclonal antibody (Chiron Diagnostics Corp. Clone 90-1A11) diluted to 0.4 ug/ml in phosphate buffered saline (PBS), 0.1% bovine serum albumin (BSA), pH7.4.

Standards-Human plasma spiked with theophylline at concentrations of 0, 1.25, 2.5, 5, 10 ug/ml.

Tracer-Dimethylacridinium ester conjugated to theophylline.

Solid phase-Monoclonal anti-allotype Igh1$^a$(Chiron Diagnostics Corp. clone 229-2D1, ATCC HB-12350) coupled to paramagnetic particles (PMP) at a ratio of 160 mg monoclonal antibody/gram of PMP; or Goat anti-Mouse Ig (polyclonal antisera), caprylic acid cut, coupled to paramagnetic particles at a ratio of 160 mg polyclonal antisera/gram of PMP. Particles were diluted to 1 mg/ml in PBS, 0.1% BSA for use in the assay.

Assay

Five microliters of theophylline standard, one hundred microliters of tracer, one hundred microliters of PBS buffer and three hundred microliters of primary antibody were sequentially pipetted into a test tube in duplicate. Reagents were mixed, and the reaction was incubated from five minutes at 37° C. One hundred microliters of particles were added, mixed and incubated for an additional 2.5 minutes at 37° C. Particles were magnetically separated and washed twice with five hundred microliters of PBS, 0.05% Triton X-100. Particles were resuspended in 100 ul of deionized water, and chemiluminescence, in relative light units (RLU), was measured using a Magic Lite Analyzer 2 (Chiron Corporation). Mean RLUs for each standard were calculated. RLUs for each standard (%Bstd.) were compared to those obtained for the 0 standard (% BOstd.) (%Bstd/BOstd).

Results

Figure 2:
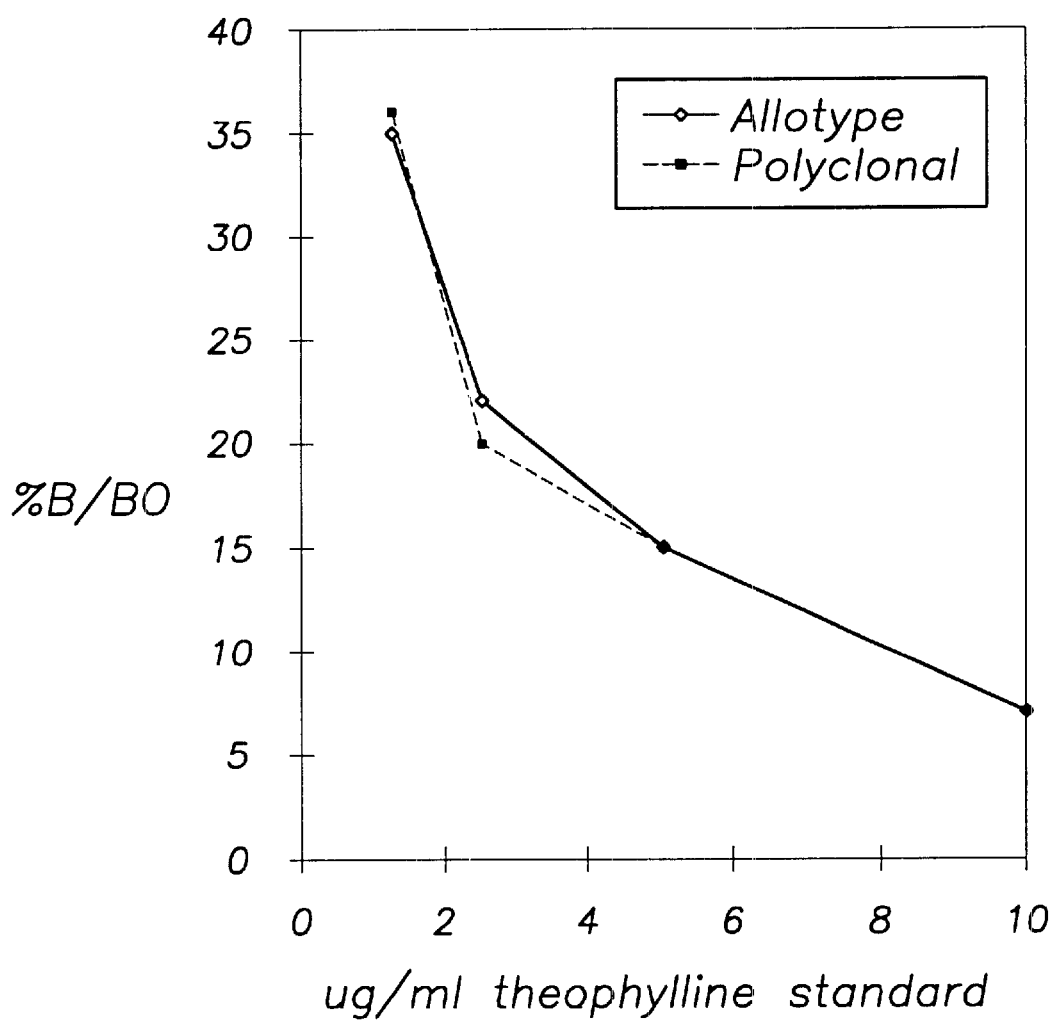
FIG. 2 is a graph of the normalized binding curves for an immunoassay for theophylline levels in a sample using polyclonal antisera (dotted line) as the capture antibodies, and anti-allotype monoclonal antibodies (solid line) as capture antibodies.

Standard curves obtained using anti-allotype PMP and goat anti-mouse Ig-PMP are shown in Table 1 and FIG. 2.

TABLE 1

Theophylline Standard Curves.

| Theophylline Standard | Anti-allotype-PMP | | Gt anti-Mouse IgPMP | |
|---|---|---|---|---|
| (ug/ml) | (Mean RLU) | % B/BO | (Mean) | % B/BO |
| 0 | 1108901 | | 842232 | |
| 1.25 | 388273 | 35 | 299768 | 36 |
| 2.5 | 243655 | 22 | 170942 | 20 |
| 5.0 | 162135 | 15 | 125709 | 15 |
| 10 | 78277 | 7 | 56718 | 7 |

Normalized binding curves are depicted in FIG. 2.

Conclusion

Anti-allotype solid phase performs comparably to polyclonal goat anti-mouse Ig-PMP in this assay format.

Interference of Anti-mouse antibodies in theophylline immunoassay and elimination of interference by adding IgG from allotype mismatched strain:

Purpose: To determine the effects of anti-mouse Ig antibodies on the accuracy of the theophylline assay. As a model for human anti-mouse Ig (HAMA), which is found in a significant number of clinical samples, goat anti-mouse Ig was added to the assay to determine the effect on the immunoassay. To eliminate the interference, mouse IgG from a strain of mouse that has a different and non-crossreacting allotype from that of the primary antibody was added to the tracer buffer.

Materials and Methods

Reagents

Primary anti-theophylline monoclonal antibody (Chiron Diagnostics corp. Clone 90-1A11) diluted to 0.4 ug/ml in PBS 0.1% BSA, pH7.4.

Standards-Human plasma spiked with theophylline at concentration of 0,1.25,2.5,5, 10 ug/ml.

Tracer-Dimethylacridinium ester conjugated to theophylline diluted in PBS, 0.1% BSA buffer.

Goat IgG (Sigma) diluted in PBS, 0.1% BSA to 10 ug/ml.

Goat anti-mouse Ig (H&L, Bio-rad) diluted to 10 ug/ml in PBS, 0.1% BSA.

SJL IgG (Chiron Diagnostics Corp. Clone 216-18D9) was added to the tracer at a final concentration of 200 ug/ml.

Solid phase-Monoclonal anti-allotype Igh1$^a$ (Chiron Diagnostics Corp. clone 229-2D1, ATCC HB-12350) coupled to paramagnetic particles at a ratio of 160 mg monoclonal/gram of PMP; or Goat anti-Mouse Ig, caprylic acid cut, coupled to paramagnetic particles at a ratio of 160 mg polyclonal/gram of PMP. Particles were diluted to 1 mg/ml in PBS, 0.1% BSA for use in the assay.

Assay

Five microliters of theophylline standard, one hundred microliters of goat IgG or goat anti-mouse Ig, one hundred microliters of tracer, and three hundred microliters of primary antibody were sequentially pipetted into a test tube in duplicate. Reagents were mixed and the reaction was incubated for five minutes a 37° C. One hundred microliters of particles were added, mixed and incubated for an additional 2.5 minutes at 37° C. Particles were magnetically separated and washed twice with five hundred microliters of PBS, 0.05% Triton X-100. Particles were resuspended in 100 $\mu$l of deionized water and chemiluminescence, in relative light units (RLU), was measured using a Magic Lite Analyzer 2. Mean RLU for each standard were calculated. RLUs for each standard were compared to those obtained for the 0 standard (%Bstd/BOstd). To determine the interference of the goat anti-mouse Ig on the assay, theophylline doses for standards plus 1 $\mu$g of goat anti-mouse Ig were determined from the standard curve.

Results

Addition of 1 $\mu$g of goat anti-mouse Ig to either theophylline immunoassay, using anti-allotype PMP or polyclonal goat anti-mouse Ig as the secondary or capture antibodies, produced an apparent increase the in dose in the standard run (Table 2).

TABLE 2

Addition of Goat anti-Mouse Ig (HAMA analog) produces an increase in theophylline dose.

| | Anti-allotype PMP | | Goat anti-mouse IgG PMP | |
|---|---|---|---|---|
| Theophylline std. | Mean RLU | % B/BO | Mean RLU | % B/BO |
| γ(+1 ug GIgG) | | | | |
| 0 ug/ml | 894778 | | 888717 | |
| 1.25 | 369262 | 41 | 396695 | 44 |
| 2.5 | 220952 | 25 | 223128 | 25 |
| 5 | 144690 | 16 | 156805 | 16 |
| 10 | 72528 | 8 | 70453 | 8 |

TABLE 2-continued

Addition of Goat anti-Mouse Ig (HAMA analog) produces an increase in theophylline dose.

| Theophylline std. | Anti-allotype PMP | | Goat anti-mouse IgG PMP | |
|---|---|---|---|---|
| | Mean RLU | % B/BO | Mean RLU | % B/BO |
| (+1 ug GAMIg) | Theophylline dose measured (μg/ml) | | Theophylline dose measured (μg/ml) | |
| 0 ug/ml | 806178 | 0.1 | 687693 | 0.4 |
| 1.25 | 293743 | 1.7 | 263157 | 2.0 |
| 2.5 | 197224 | 3.0 | 174958 | 4.1 |
| 5 | 110440 | 6.8 | 101082 | 7.7 |
| 10 | 57726 | >10 | 53919 | >10 |

Dose recovery for the theophylline standards was determined by calculating:

% Recovery=dose obtained in the presence of Gt anti-mouse Ig×100 expected dose (nominal standard value)

Using both solid phases, apparent dose recoveries were greater than 100% when the goat anti-mouse Ig was added to the assay. (Table 3). Over recovery of dose was greater for the assay using the polyclonal PMP than for the assay using the anti-allotype PMP.

TABLE 3

Standard dose recoveries in the presence of Goat anti-mouse Ig

| Anti-Allotype PMP | | | Goat anti-mouse Ig PMP | | |
|---|---|---|---|---|---|
| Expected dose | Observed dose | % Recovery | Expected dose | Observed dose | % Recovery |
| 1.25 ug/ml | 1.7 ug/ml | 136 | 1.25 ug/ml | 2.0 ug/ml | 160 |
| 2.5 ug/ml | 3.0 ug/ml | 120 | 2.5 ug/ml | 4.1 ug/ml | 164 |
| 5 ug/ml | 6.8 ug/ml | 136 | 5.0 ug/ml | 7.7 ug/ml | 154 |
| 10 ug/ml | >10 ug/ml | >100 | 10 ug/ml | >10 ug/ml | >100 |

To eliminate the interference by goat anti-mouse Ig (HAMA analog) in the theophylline assay, 20 μg of IgG$_1$, from a hybridoma produced from an SJL mouse, were added per test in the tracer buffer. As shown in Table 4, recovery doses in the presence of the goat anti-mouse Ig were lowered to more accurate levels in the theophylline assay run with the anti-allotype solid phase. In marked contrast, recovery of theophylline standard doses in the assay using the goat anti-mouse Ig PMP, continued to increase.

TABLE 4

Effect of addition of SJL IgG to theophylline assay

| Theophylline std. | Anti-allotype PMP | | Goat anti-mouse IgG PMP | |
|---|---|---|---|---|
| | Mean RLU | % B/BO | Mean RLU | % B/BO |
| (+1 ug GIgG) | | | | |
| 0 | 894778 | | 888717 | |
| 1.25 | 369262 | 41 | 396695 | 44 |
| 2.5 | 220952 | 25 | 223128 | 25 |
| 5 | 144690 | 16 | 156805 | 16 |
| 10 | 72528 | 8 | 70453 | 8 |

TABLE 4-continued

Effect of addition of SJL IgG to theophylline assay

| Theophylline std. | Anti-allotype PMP | | Goat anti-mouse IgG PMP | |
|---|---|---|---|---|
| | Mean RLU | % B/BO | Mean RLU | % B/BO |
| (+1 ug GAMIg + 20 ug SJL) | Theophylline dose measured (μg/ml) | | Theophylline dose measured (μg/ml) | |
| 0 | 864599 | 0.08 | 301129 | 1.7 |
| 1.25 | 355780 | 1.3 | 98192 | 7.9 |
| 2.5 | 215413 | 2.6 | 68091 | 9.8 |
| 5 | 137693 | 5.3 | 41605 | >10 |
| 10 | 72612 | 9.8 | 26822 | >10 |

Percent dose recoveries for theophylline standards run in the presence of goat anti-mouse Ig and SJL IgG$_1$ are shown in Table 5. Average recovery for standard doses in the theophylline assay was 103% for the anti-allotype solid phase and ranged from 200–624% for the goat anti-mouse Ig solid phase.

TABLE 5

Percent dose recoveries for theophylline standards run in the presence of goat anti-mouse Ig (HAMA analog) and SJL IgG$_1$

| Anti-Allotype PMP | | | GAMIg PMP | | |
|---|---|---|---|---|---|
| Expected dose | Observed dose | % Recovery | Expected dose | Observed dose | % Recovery |
| 1.25 ug/ml | 1.3 ug/ml | 104 | 1.25 ug/ml | 7.8 ug/ml | 624 |
| 2.5 ug/ml | 2.6 ug/ml | 104 | 2.5 ug/ml | 9.8 ug/ml | 392 |
| 5 ug/ml | 5.3 ug/ml | 106 | 5.0 ug/ml | >10 ug/ml | >200 |
| 10 ug/ml | 9.8 ug/ml | 98 | 10 ug/ml | >10 ug/ml | >100 |

Discussion

Human anti-mouse immunoglobulins (HAMA) present in human serum/plasma samples have been shown to cause interferences in immunoassays that utilize murine monoclonal antibodies. This interference is manifested by the inaccurate determination of a particular analyte present in the patient sample. This inaccuracy can lead to a misdiagnosis of the patient. To circumvent this problem, most immunoassays contain large quantities of mouse serum or mouse Ig to block the HAMA from binding to the specific monoclonal antibody that is critical to the assay. However, when immunoassays rely on species-specific antibody, e.g., goat anti-mouse Ig, to capture specific immune complexes, addition of nonspecific mouse Ig is not a viable alternative.

A model system of theophylline immunoassay was developed which utilizes a highly specific monoclonal antibody to an allotypic determinant on the anti-theophylline (primary) antibody to capture immune complexes formed during the assay. The anti-allotypic monoclonal antibody was coupled to paramagnetic particles and used as a solid phase in a chemiluminescent immunoassay to quantitate theophylline levels in human plasma This assay was compared to a chemiluminescent assay which utilized a polyclonal goat anti-mouse IgG capture antibody coupled to paramagnetic particles as a solid phase.

Both immunoassays were sensitive to the presence of goat anti-mouse Ig, which was added to the assay to mimic the presence of HAMA in human patient specimen. The results suggest that the assay that utilized the anti-allotype solid phase was slightly less sensitive to the interference. In both assays, theophylline doses of the standards were increased. An error in determining the exact amount of drug in a patient specimen might cause a physician to change patient dosage, with detrimental effects.

Because the anti-allotype monoclonal antibody is so specific, one can eliminate the effects of the interference of anti-mouse immunoglobulins by adding nonspecific Ig from a mouse strain that does not share allotypic determinants which the primary anti-theophylline antibody. This was achieved in the theophylline immunoassay by adding IgG from an SJL mouse. When the SJL IgG was added to the assay, theophylline doses for the standards did not over recover. In contrast, the interference effect of anti-mouse Ig in the theophylline assay using the polyclonal solid phase could not be overcome with the addition of nonspecific mouse IgG and in fact, exacerbated the problem.

EXAMPLE 3

DHEA S Immunoassay using Anti-allotype Solid Phase

Purpose. To use an anti allotype monoclonal antibody coupled to paramagnetic particles to separate bound analyte from free analyte using a dehydroepiandrosterone sulfate (DHEA-S) assay as a model system.

Materials and Methods

Reagents

Primary antiDHEA-S monoclonal antibody (Chiron Diag. Clone SS165-9A 11) diluted to 0.2 μg/ml in PBS, 0.1%BSA, pH7.4

Standards-DHEA-S diluted in PBS,0.1%BSA, pH 7.4 at 10, 50, 100 and 250 ng/ml Tracer-Dimethylacridinium ester conjugated to DHEA-S Solid phase-Monoclonal anti-allotype Igh4$^b$(Chiron Diag. Clone 240-10C12) coupled to paramagnetic particles at a ratio of 160 mg monoclonal/gram of PMP or goat-anti-mouse Ig caprylic acid cut, coupled to paramagnetic particles at a ratio of 160 mg polyclonal/gram of PMP. Particles were diluted to 100 μg/ml in PBS, 0.1%BSA for use in the assay.

Assay

Twenty five microliters of DHEA-S standard, one hundred microliters of tracer, one hundred microliters of buffer and one hundred microliters of primary antibody were sequentially pipetted into a test tube in duplicate. Reagents were mixed and the reaction was incubated for five minutes at 37° C. Five hundred microliters of particles were added, mixed and incubated for an additional 2.5 minutes at 37° C. Particles were magnetically separated and washed twice with five hundred microliters of PBS, 0.05%Triton X-100. Particles were resuspended in 100 μl of dH20 and chemiluminescence, in relative light units (RLU), was measured using a Magic Lite Analyzer 2. Mean RLU for each standard were calculated RLUs for each standard were compared to those obtained fro the 0 standard (%Bstd/BOstd).

Results

Figure 3:
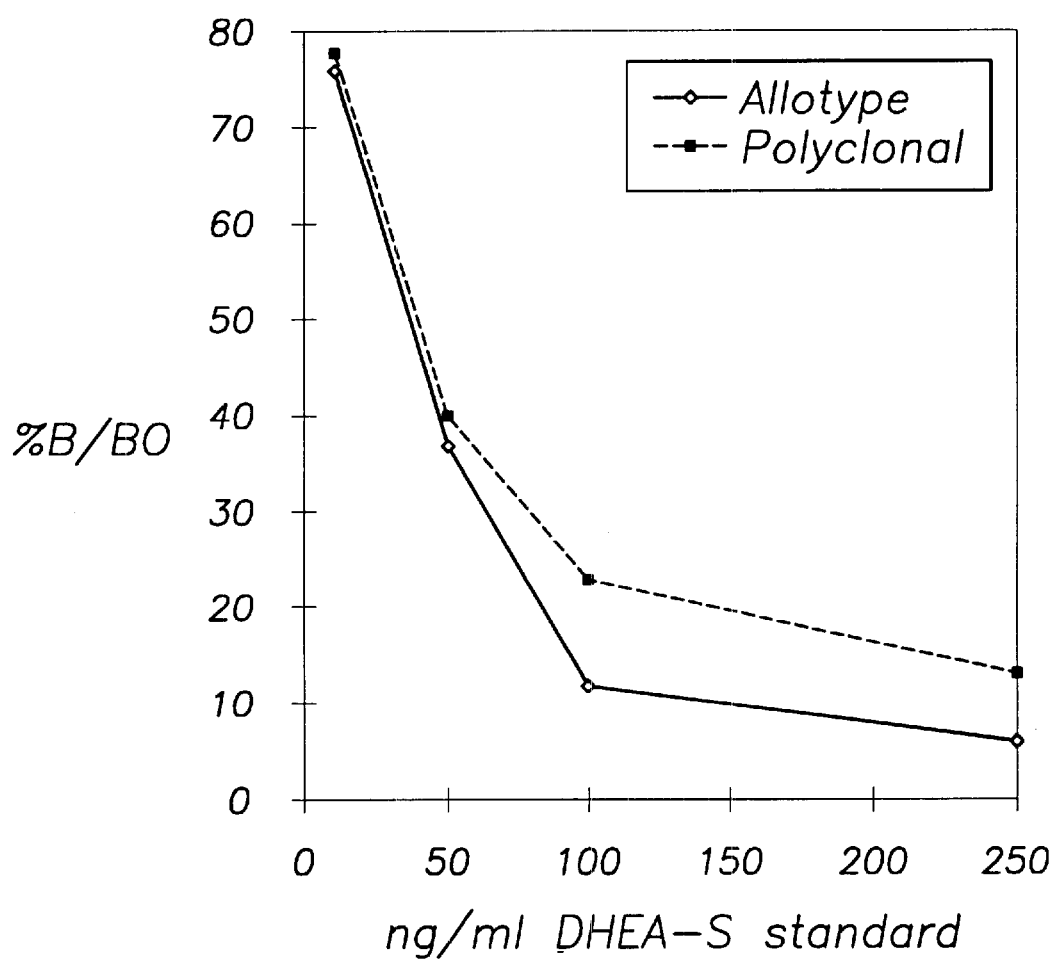
FIG. 3 is a graph of the normalized binding curves for an immunoassay for DHEA-S in a sample using polyclonal antisera (dotted line) as the capture antibodies, and anti-allotype monoclonal antibodies (solid line) as capture antibodies.

DHEA-S standard curves obtained using anti-allotype PMP and goat anti-mouse Ig-PMP are shown in Table 6 and FIG. 3.

TABLE 6

DHEA-S Standard Curves

| DHEA-S Standard (μg/ml) | Anti-allotype-PMP (Mean RLU) | % B/BO | Gt anti-Mouse IgPMP (Mean RLU) | % B/BO |
| --- | --- | --- | --- | --- |
| 0 | 770603 | | 727373 | |
| 10 | 588062 | 76 | 568380 | 78 |
| 50 | 284954 | 37 | 288504 | 40 |
| 100 | 91088 | 12 | 170228 | 23 |
| 250 | 50526 | 6 | 96639 | 13 |

Normalized binding curves are depicted in FIG. 3.

Conclusion

Anti-allotype solid phase comparably to polyclonal goat anti-mouse Ig-PMP.

Interference of Anti-mouse antibodies in DHEA-S immunoassay and elimination of interference by adding IgG from allotype mismatched strain.

Purpose: To determine the effects of anti-mouse Ig antibodies on the DHEA-S assay. As a model for human anti-mouse Ig, which is found in a significant number of clinical samples, goat anti-mouse IgFc was added to the assay to determine the effect. To eliminate the interference, using IgG from a strain of mouse that has a different and noncrossreacting allotype from that of the primary antibody was added to the tracer buffer.

Materials and Methods

Reagents

Primary anti-DHEA-S monoclonal antibody (Chiron Diag. Clone SS165-9A11) diluted to 0.2 g/ml in PBS, 0.1%BSA, pH7.4

Standards-DHEA-S diluted in PBS,0.1%BSA at concentration of 10,20,100,250 ng/ml

Tracer-Dimethylacridinium ester conjugated to DHEA-S diluted in PBS,0.1%BSA buffer Goat IgG (Sigma) diluted in PBS,0.1%BSA to 10 μg/ml Goat anti-mouse Ig Fc(Cappel) diluted to 10 μg/ml in PBS,0.1%BSA A/J IgG (Chiron Diag. Clone 126-12C3) was added to the tracer at a final concentration of 200 μg/ml Solid phase-Monoclonal anti-allotype Igh4$^b$ (Chiron Diag. Clone 240-10C12) coupled to paramagnetic particles at a ratio of 160 mg monoclonal/gram of PMP or Goat anti-Mouse Ig, caprylic acid cut, coupled to paramagnetic particles at a ratio of 160 mg polyclonal/gram of PMP. Particles were diluted to 125 μg/ml in PBS,0.1%BSA for use in the assay.

Assay

Twenty five microliters of DHEA-S standard, one hundred microliters of Goat IgG or Goat anti-mouse IgFc, one hundred microliters of tracer, and one hundred microliters of primary antibody were sequentially pipetted into a test tube in duplicate. Reagents were mixed and the reaction was incubated for five minutes at 37° C. Five hundred microliters of particles were added, mixed and incubated for an additional 2.5 minutes at 37° C. Particles were magnetically separated and washed twice with five hundred microliters of PBS, 0.05% Triton X-100. Particles were resuspended in 100 μl of dH20 and chemiluminescence, in relative light units (RLU), was measured using a Magic Lite Analyzer 2. Mean RLU for each standard were calculated. RLUs for each standard were compared to those obtained for the 0 standard (%Bstd/Bostd). To determine the interference of the goat anti-mouse IgFc on the assay, DHEA-S dose for standards plus 1 μg of goat anti-mouse IgFc were determined from the standard curve.

Results

Addition of 1 µg of goat anti-mouse Ig to either DHEA-S immunoassay, using anti-allotype PMP or polyclonal goat anti-mouse Ig, produced an apparent increase in dose in the standard run. (Table 7)

TABLE 7

Addition of Goat anti-Mouse Ig (HAMA analog) produces an increase in DHEA-S dose

|  | Anti-allotype-PMP | | Goat anti-mouse IgGPMP | |
|---|---|---|---|---|
| DHEA-S Std | (Mean RLU) | % B/BO | (Mean RLU) | % B/BO |
| (+1 µg GIgG) | | | | |
| 0 | 362338 | | 391450 | |
| 10 | 250819 | 69 | 265884 | 68 |
| 50 | 122070 | 34 | 123851 | 32 |
| 100 | 79728 | 22 | 88043 | 22 |
| 250 | 44699 | 12 | 52055 | 13 |
| (+1 µg GAMIgFc) | | DHEA-S dose | | DHEA-S dose |
| 0 | 304672 | 4.0 | 247330 | 12.4 |
| 10 | 206558 | 17.6 | 172734 | 27 |
| 50 | 99541 | 69.8 | 77347 | 129 |
| 100 | 64698 | 139.6 | 48709 | >250 |
| 250 | 37763 | >250 | 26180 | 250 |

Dose recovery for the DHEA-S standards was determined by calculating:

%Recovery=dose obtained in the presence of Gt anti-mouse IgFc× 100 expected dose (nominal standard value)

Using both solid phases, dose recoveries were greater than 100% when the goat anti-mouse IgFc was added to the assay. (Table 8) Over recovery of dose was greater for the polyclonal PMP than the anti-allotype PMP

TABLE 8

Standard dose recoveries in the presence of Goat anti-mouse IgFc

| Anti-Allotype PMP | | | Goat anti-mouse Ig PMP | | |
|---|---|---|---|---|---|
| Expected dose | Observed dose | % Recovery | Expected dose | Observed dose | % Recovery |
| 10 ng/ml | 17.6 ng/ml | 176 | 10 ng/ml | 27 ng/ml | 270 |
| 50 ng/ml | 69.8 ng/ml | 140 | 50 ng/ml | 129.1 ng/ml | 258 |
| 100 ng/ml | 139.6 ng/ml | 140 | 100 ng/ml | >250 ng/ml | >250 |
| 250 ng/ml | >250 ng/ml | >100 | 250 ng/ml | >250 ng/ml | >100 |

To eliminate the interference by goat anti-mouse IgFc (HAMA analog) in the DHEA-S assay, 20 µg of IgG$_1$, from a hybridoma produced from an A/J mouse, was added per test in the tracer buffer. Tracer, which contained the A/J IgG, was added to the sample, which contained DHEA-S and goat anti-mouse IgGFc (HAMA analog), and incubated for 5 minutes at 37° C. The primary anti-DHEA-S monoclonal antibody was then added and the reaction incubated for an additional five minutes at 37° C. Solid phase, either anti-allotype PMP or Goat anti-mouse Ig PMP, was added and incubated for 2.5 minutes at 37° C. As shown in Table 9, standard doses in the presence of the goat anti-mouse IgFc were lowered to acceptable levels in the DHEA-S assay run with the anti-allotype solid phase. In marked contrast, DHEA-S standard doses, in the assay using the goat anti-mouse IgPMP, continued to increase.

TABLE 9

Effect of addition of A/J IgG to DHEA-S assay

|  | Anti-allotype-PMP | | Goat anti-mouse IgGPMP | |
|---|---|---|---|---|
| DHEA-S Std | (Mean RLU) | % B/BO | (Mean RLU) | % B/BO |
| (+1 µg GIgG) | | | | |
| 0 | 894778 | | 391450 | |
| 10 | 369262 | 69 | 265884 | 68 |
| 50 | 220952 | 34 | 123851 | 32 |
| 100 | 144690 | 22 | 88043 | 22 |
| 250 | 72528 | 12 | 52055 | 13 |
| (+1 µg GAMIgFc) | | DHEA-S dose | | DHEA-S dose |
| 0 | 361846 | 0.4 | 48194 | >250 |
| 10 | 251808 | 9.9 | 37094 | >250 |
| 50 | 122322 | 49.9 | 20677 | >250 |
| 100 | 724923 | 115.3 | 19352 | >250 |
| 250 | 40796 | >250 | 16954 | >250 |

Percent dose recoveries for DHEA-S standards run in the presence of goat anti-mouse Ig and A/J IgG$_1$ are shown in Table 10. Average recovery for standard doses in the DHEA-S assay was 105% for the anti-allotype solid phase and ranged from 200–>2500% for the goat anti-mouse Ig solid phase.

TABLE 10

Percent dose recoveries for DHEA-S standards run in the presence of goat anti-mouse IgFc (HAMA analog) and A/J IgG)

| Anti-Allotype PMP | | | GAMIg PMP | | |
|---|---|---|---|---|---|
| Expected dose | Observed dose | % Recovery | Expected dose | Observed dose | % Recovery |
| 10 ng/ml | 9.9 ng/ml | 99 | 10 ng/ml | >250 ng/ml | >2500 |
| 50 ng/ml | 49.9 ng/ml | 100 | 50 ng/ml | >250 ng/ml | >500 |
| 100 ng/ml | 115 ng/ml | 115 | 100 ng/ml | >250 ng/ml | >250 |
| 250 ng/ml | >250 ng/ml | >100 | 250 ng/ml | >250 ng/ml | >100 |

Discussion

Anti-mouse immunoglobulins (HAMA) present in human serum/plasma samples have been shown to cause interferences in immunoassays that utilize murine monoclonal antibodies. This interference is manifested by the inaccurate determination of a particular analyte present in the patient sample. This inaccuracy can lead to a misdiagnosis of the patient. To circumvent this problem, most immunoassays contain large quantities of mouse serum or mouse Ig to block the HAMA from binding to the specific monoclonal antibody that is critical to the assay. However, when immunoassays rely on species specific antibody, i.e. goat anti-mouse Ig, to capture specific immune complexes addition of non-specific mouse Ig is not a viable alternative.

A model system of DHEA-S immunoassay was developed which utilizes a highly specific monoclonal antibody to an allotypic determinant on the anti-DHEA-S(primary) antibody to capture immune complexes formed during the assay. The anti-allotypic monoclonal antibody was coupled to paramagnetic particles and used as a solid phase in a chemiluminescent immunoassay to quantitate DHEA-S in human plasma. This assay was compared to a chemiluminescent assay which utilized a polyclonal goat anti-mouse IgG coupled to paramagnetic particles as a solid phase.

Both immunoassays were sensitive to the presence of goat anti-mouse IgFc, which was added to the assay to mimic the presence of HAAMA in patient specimen. The results suggest that the assay that utilized the anti-allotype solid phase was slightly less sensitive to the interference. In both assays, DHEA-S doses of the standards were increased. An error in determining the exact amount of hormone in a patient specimen might cause a physician to change patient diagnosis, with detrimental effects.

Because the anti-allotype monoclonal antibody is so specific, one can eliminate the effects of the interference of anti-mouse immunoglobulins by adding nonspecific Ig from a mouse strain that does not share allotypic determinants with the primary anti-DHEA-S antibody. This was achieved in the DHEA-S immunoassay by adding IgG from an A/J mouse. When the A/J IgG was added to the assay, DHEA-S doses for the standards did not over recover. In contrast, the interference effect of an anti-mouse Ig in the DHEA-S assay using the polyclonal solid phase could not be overcome with the addition of nonspecific mouse IgG and, in fact, exacerbated the problem.

EQUIVALENTS

From the foregoing description, one skilled in the art can easily ascertain the essential characteristics of this invention, and without departing from the spirit and scope thereof, can make various changes and modifications to adapt it to various usages and conditions. Such embodiments are intended to be included within the scope of the following claims.

What is claimed is:

1. A method for determining an amount of analyte in a patient sample, said method comprising:
   a. combining the patient sample with a binding protein specific for said analyte, and detectably labeled tracer molecules specific for said binding protein, wherein said detectably labeled tracer molecules comprise a detectable label and have a specific affinity for said primary binding protein;
   b. incubating the combination formed in step (a) under conditions which permit the analyte and the labeled tracer molecules to bind to said binding protein;
   c. contacting the combination formed in step (a) with a solid phase having immobilized thereon a capture antibody specific for the binding protein allotype;
   d. incubating the combination formed in step (c) under conditions which permit the binding protein to bind with the capture antibody;
   e. separating the solid phase from the sample; and
   f. detecting the labeled tracer molecules bound to the solid phase;
   wherein the amount of labeled tracer detected is indicative of the amount of analyte present in the sample.

2. The method of claim 1 wherein the binding protein comprises an antibody or receptor.

3. The method of claim 2 wherein the binding protein is an immunoglobulin of the subtype G, M, A or E.

4. The method of claim 3 wherein the binding protein is an immunoglobulin G isotype.

5. The method of claim 1, wherein the binding protein is derived from a species selected from the group consisting of mouse, rabbit, goat, sheep, guinea pig and human.

6. The method of claim 5 wherein the binding protein and the capture antibody are of mouse origin.

7. The method of claim 1 wherein the patient sample is serum, plasma, urine, lymphatic fluid, cerebrospinal fluid, or tissue.

8. The method of claim 1 wherein the detectable label is a chemiluminescent label, a fluorescent label, an enzyme or a radioisotope.

9. The method of claim 8 wherein the label is an acridinium ester.

10. The method of claim 1 wherein the solid phase is a magnetic particle, bead, membrane, tray or test tube.

11. The method of claim 1 wherein the labeled tracer molecules comprise analyte molecules conjugated with a detectable label.

12. The method of claim 11 wherein the tracer molecules compete with analyte in the sample to bind with the binding protein.

13. The method of claim 1 further comprising adding to the combination in step (a) an antibody having an allotype different from the binding protein allotype, which allotype is not recognized by the capture antibody of step (c).

14. The method of claim 13 wherein the antibody having an allotype different from the binding protein allotype has the same isotype as the binding protein.

15. The method of claim 13 wherein the antibody having an allotype different from the binding protein allotype is derived from a mouse strain which is the same as the mouse strain from which the capture antibody is derived.

16. The method of claim 1 wherein the analyte is dehydrepiandrosterone sulfate or theophylline.

17. The method of claim 1 wherein the capture antibody is specific for an allotypic determinant present on the binding protein.

18. The method of claim 17 wherein the capture antibody is obtained from hybridoma cell line ATCC HB-12349.

19. The method of claim 17 wherein the capture antibody is obtained from hybridoma cell line ATCC HB-12350.

20. A method for determining an amount of analyte in a patient sample, said method comprising:
   a. combining the patient sample with an amount of primary monoclonal antibody and a tracer comprising acridinium-ester-labeled analyte molecules specific for said primary antibody;
   b. incubating the combination formed in step (a) under conditions which permit the analyte and the tracer to bind to said primary antibody;
   c. contacting the combination of step (a) with a paramagnetic particle having immobilized thereon a capture anti-allotypic monoclonal antibody specific for the primary monoclonal antibody allotype;
   d. incubating the combination formed in step (c) under conditions which permit the primary monoclonal antibody to bind with the capture antibody;
   e. separating the solid phase from the sample, unbound tracer and unbound analyte; and
   f. detecting the tracer bound to the solid phase; wherein the amount of detected tracer is indicative of the amount of analyte present in the sample.

21. The method of claim 20 wherein the primary antibody and the capture antibody both are derived from mouse.

22. The method of claim 20 further comprising adding to the sample prior to step (a) an excess over the amount of the primary antibody of mouse antibodies having an isotype which is the same as the isotype of the primary antibody.

23. The method of claim 22 wherein the mouse antibodies having an isotype which is the same as the isotype of the primary antibody are derived from a mouse strain which is the same as the mouse strain from which the capture antibodies are derived.

24. The method of claim 22 wherein the mouse antibodies having an isotype which is the same as the isotype of the primary antibody are preincubated with the patient sample.

* * * * *